(12) United States Patent
Åkerfeldt

(10) Patent No.: US 7,247,163 B2
(45) Date of Patent: Jul. 24, 2007

(54) INTERNAL TELESCOPIC GUIDE FOR AN INFLATABLE AIR CUSHION

(75) Inventor: Dan Åkerfeldt, Uppsala (SE)

(73) Assignee: Radiamedical Systems AB, Uppsala (SE)

( * ) Notice: Subject to any disclaimer, the term of this patent is extended or adjusted under 35 U.S.C. 154(b) by 133 days.

(21) Appl. No.: 10/209,974

(22) Filed: Aug. 2, 2002

(65) Prior Publication Data

US 2004/0024417 A1 Feb. 5, 2004

(51) Int. Cl.
*A61B 17/00* (2006.01)

(52) U.S. Cl. .................. 606/203; 606/201; 606/151

(58) Field of Classification Search .............. 606/1, 606/201, 203, 151
See application file for complete search history.

(56) References Cited

U.S. PATENT DOCUMENTS

| | | | | |
|---|---|---|---|---|
| 3,193,239 A | * | 7/1965 | Monroe | 248/566 |
| 3,797,853 A | * | 3/1974 | Grosch et al. | 280/740 |
| 4,605,203 A | * | 8/1986 | Hooper et al. | 254/93 HP |
| 5,307,811 A | | 5/1994 | Sigwart et al. | |
| 5,542,427 A | | 8/1996 | Akerfeldt | |
| 5,792,173 A | * | 8/1998 | Breen et al. | 606/201 |
| 5,921,532 A | * | 7/1999 | Pierce et al. | 267/64.19 |
| 5,997,564 A | * | 12/1999 | Shehata et al. | 606/201 |
| 6,066,157 A | * | 5/2000 | Barbere | 606/194 |
| 6,082,708 A | * | 7/2000 | Mullican et al. | 254/93 HP |
| 6,174,306 B1 | * | 1/2001 | Fleischmann | 604/543 |
| 6,264,673 B1 | * | 7/2001 | Egnelov et al. | 606/201 |
| 7,135,032 B2 | * | 11/2006 | Akerfeldt | 606/203 |

FOREIGN PATENT DOCUMENTS

| | | |
|---|---|---|
| EP | 0 462 088 B1 | 12/1991 |
| SU | 1386172 A1 | 4/1988 |
| WO | WO 94/05221 A1 | 3/1994 |
| WO | WO 98/34547 A1 | 8/1998 |
| WO | WO 01/85062 A1 | 11/2001 |

OTHER PUBLICATIONS

U.S. Appl. No. 09/355,736, filed Oct. 21, 1999, Sjorgen et al.

* cited by examiner

*Primary Examiner*—Anhtuan T. Nguyen
*Assistant Examiner*—Darwin P. Erezo
(74) *Attorney, Agent, or Firm*—Foley & Lardner LLP

(57) ABSTRACT

The invention provides an air cushion unit (4) for use in conjunction with a compression device for stopping bleeding from puncture wounds. The air cushion unit (4) comprises a base plate (5), an inflatable air cushion (6), which is attached to the base plate (5), and an internal telescopic guide (7), the first end of which is attached to the base plate (5) and the second end of which is attached to the top of the air cushion (6). Throughout the pressurizing of the inflatable air cushion (6), the length of the telescopic guide (7) corresponds to the degree of expansion of the air cushion (6), thereby providing an internal support for the air cushion unit (4), which eliminates undesired, irregular movements of the air cushion (6).

20 Claims, 2 Drawing Sheets

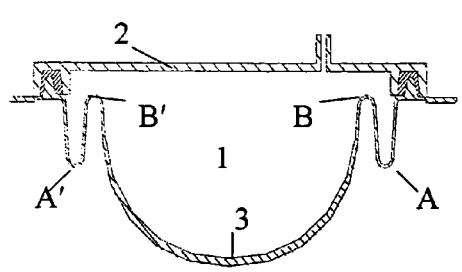
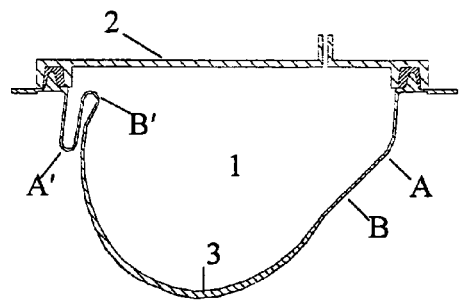
Fig. 1 (Prior art)　　　Fig. 2 (Prior art)
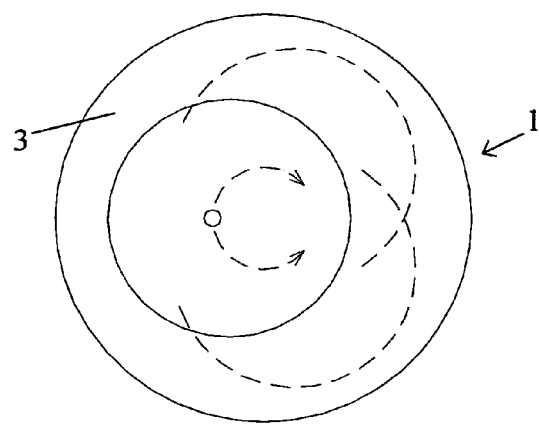
Fig. 3 (Prior art)
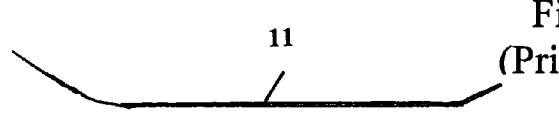
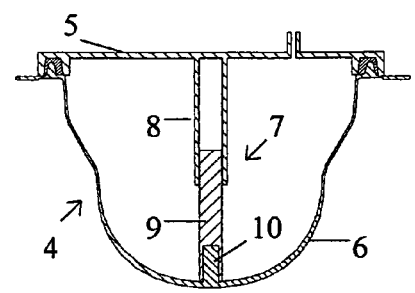
Fig. 4　　　Fig. 5

INTERNAL TELESCOPIC GUIDE FOR AN INFLATABLE AIR CUSHION

BACKGROUND OF THE INVENTION

The present invention relates generally to air cushion units used in conjunction with compression devices for stopping bleeding from puncture wounds, and in particular to an inflatable air cushion unit being provided with a telescopic guide which ensures that the air cushion during pressurizing unfolds regularly, thereby preventing the contact area of the air cushion from moving away from the wound site.

The present invention is an improvement of the air cushion units disclosed in the present applicant's WO94/05221, U.S. Pat. No. 5,542,427 and WO98/34547 publication, where the latter discloses air cushions provided with a reinforcement portion. The air cushion unit according to these publications includes a base plate, the upper side of which is attached to the arch of a femoral compression device, such as the femoral compressor disclosed in EP 0 462 088 and U.S. Pat. No. 5,307,811, which are assigned to the present applicant. On the base plate there is an inflatable air cushion, which is mounted by gluing or fusing along the circumference of the base place to provide an airtight sealing between the air cushion and the base plate. The cushion is made of a material that is folded such that the air cushion, when not inflated, i.e. when it is packaged, occupies as little volume as possible.

SUMMARY OF THE INVENTION

A potential problem with these prior art air cushions is that during the pressurizing phase they have a tendency to unfold unevenly, i.e. the folds do not unfold continuously and regularly but stepwise in an irregular way. These irregular movements of the air cushion during pressurizing may move the entire compression device away from its correct position over the femoral or other artery, which may cause unnecessary bleeding. The irregular behaviour of a compression device provided with such an air cushion unit may also give an inexperienced user a feeling that something is wrong, which—besides being uncomfortable in itself—may call for frequent checks that everything is in order, which extends the pressurizing time and may cause extra bleeding. Another problem is that the air cushion when in a semi-inflated state has a tendency to behave like a ball joint in such a way that the centre of the cushion surface moves around the wound site. In the worst case, this ball-joint movement may cause the air cushion to roll off the wound site, which again gives rise to unnecessary bleeding.

The object of the present invention is therefore to provide an improved air cushion unit that during pressurizing unfolds in a regular way without any undesired movements, which makes a compression device provided with such an air cushion unit more user-friendly and eliminates the risk that the air cushion moves away from the wound site.

This object is achieved by providing an improved air cushion unit, preferably of a single use type, for use together with a femoral (or other artery or vessel) compressor. The air cushion unit, which is to be attached to the arch (or other stiff member or flexible member such as a strap) of the femoral compressor, comprises a base plate and an inflatable air cushion attached to the base plate. According to the present invention, the air cushion unit is provided with a telescopic guide, which is arranged inside the air cushion and extends from the base plate to the top of the air cushion.

BRIEF DESCRIPTION OF THE DRAWINGS

FIG. 1 is a cross-sectional view of a prior art air cushion unit.

FIG. 2 is a cross-sectional view of the air cushion unit of FIG. 1 in a semi-inflated state, and illustrates the irregular unfolding of the air cushion.

FIG. 3 illustrates schematically the ball-joint movement of a semi-inflated air cushion according to prior art.

FIG. 4 is a cross-sectional view of an air cushion unit according to the present invention.

FIG. 5 is a cross-sectional view of the air cushion unit of FIG. 4 in an inflated state, and illustrates the regular unfolding of the air cushion.

DETAILED DESCRIPTION OF THE PREFERRED EMBODIMENTS

Figure 6:
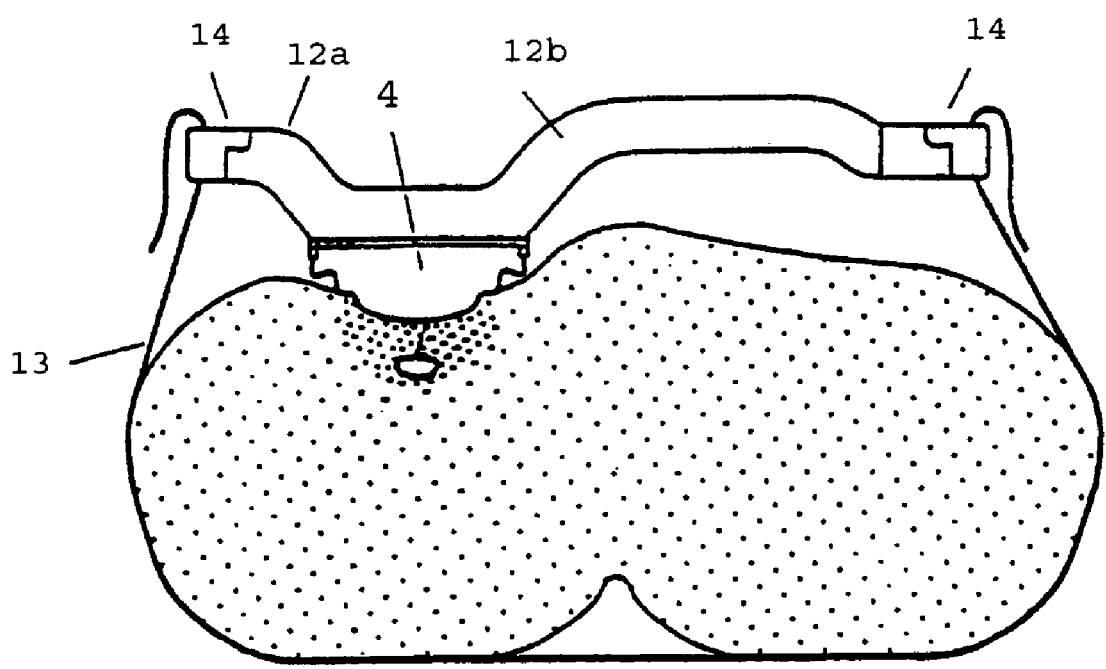
FIG. 6 is a cross-sectional of an air cushion unit being applied to a patient.

The air cushion unit according to the present invention has the same basic design as the ones disclosed in the above referenced WO 94/05221 or WO 98/34547, the main difference being that the air cushion disclosed in WO 98/34547 is provided with a reinforcement portion integral with the cushion surface. The entire contents of WO 94/05221; WO 98/34547; EP 462 088; U.S. Pat. No. 5,542,427; U.S. Pat. No. 5,307,811; and U.S. application Ser. No. 09/355,736 are incorporated herein by reference. For the sake of simplicity, the air cushion according to the present invention as well as the air cushion according to prior art are described and illustrated without this reinforcement portion, but it should be understood that such a reinforcement portion could be provided also for the present air cushion.

A prior art cushion unit 1 is illustrated in cross-section in FIG. 1 and comprises a base plate 2, on which an inflatable air cushion 3 is mounted by gluing or fusing along the periphery of the base plate 2. In use, the base plate 2 is attached to the arch (or other portion) of a femoral (or other vessel) compressor, such as the one disclosed in EP 0 462 088 and U.S. Pat. No. 5,307,811. The attachment of the cushion unit 1 to the femoral compressor is done by a snap attachment, which is fully disclosed in the above mentioned application WO 94/05221, and will therefore not be described herein. FIG. 1 shows the air cushion unit 1, which preferably is a replaceable and single use unit, in a state before use, wherein the material from which the air cushion 3 is made is folded at A, A' and B, B', so that the air cushion unit 1 occupies as little volume as possible.

FIG. 2 shows the air cushion 3 in a semi-inflated state, and illustrates the above-mentioned problem that the prior art air cushion 3 during pressurizing unfolds irregularly, which—in this particular case—makes the air cushion 3 to adapt the deformed shape shown in the figure, where the folds at A, B have been unfolded while the folds at A', B' still are intact. The irregular behaviour of the air cushion 3 is also transmitted to a femoral compressor on which the air cushion unit 1 is attached, which in the worst case may cause the femoral compressor to move away from its correct positioning over the femoral artery, thereby causing unnecessary bleeding. Even though the risk that the femoral compressor actually moves during inflation in praxis has proven to be very small, a non-negligible disadvantage with the irregular and stepwise expansion of the air cushion 3 is that it may give an inexperienced user (e.g. a nurse or a doctor) the impression that something is going wrong during the inflation procedure, which, in turn, calls for frequent (and mostly unnecessary) checks that everything is in order.

FIG. 3 is a schematic top view of the prior art air cushion unit 1 in a semi-inflated state, and illustrates schematically the above-mentioned problem that the air cushion 3 when in a semi-inflated state can move like a ball joint in that the top surface of the air cushion 3 moves around the centre of the air cushion 3. This ball joint movement, which may be in the clockwise or counter-clockwise direction, is indicated by dashed lines and by the double-arrow C. In the worst case, this undesired movement may cause the air cushion 3 to slip away from its correct positioning at the puncture site, which again leads to unnecessary bleeding or at least to additional checks that the femoral compressor, on which the air cushion unit 1 is attached, is correctly positioned at the femoral artery.

In FIG. 4 is illustrated an air cushion unit 4 according to the present invention. The air cushion unit 4 comprises a base plate 5 and an air cushion 6, which—as in the prior art design—is attached to the base plate 5 by gluing or fusing along the periphery of the base plate 5. As before, the air cushion unit 4 is designed for attachment to the arch 11 (or other portion) of a femoral (or other vessel) compressor, such as the compressor disclosed in EP 0 462 088 and U.S. Pat. No. 5,307,811. FIG. 6 shows the air cushion unit 4 attached to a patient by an arch formed by two extensions 12a and 12b. The extensions are fastened to a belt 13 via fasteners (such as a self locking device) 14. The attachment can be releasable as described in, for example, WO 94/05221. In contrast to the prior art cushion unit 1 described above, the air cushion unit 4 comprises also an internal telescopic guide 7. The telescopic guide 7, which is inside the air cushion 6 and extends from the base plate 5 to the top of air cushion 6, comprises a first rod 8 and a second rod 9. In this embodiment, the first rod 8, which extends from the base plate 5, is hollow and is made integrally with the base plate 5, while the second rod 9, which extends from the top of the air cushion 6 and into the hollow first rod 8, is attached to the air cushion by a pin 10, which projects a short distance into the otherwise solid second rod 9. The inner diameter of the first rod 8 is approximately equal to the diameter of the second rod 9.

FIG. 5 shows the air cushion 6 in an inflated state, and illustrates that the air cushion 6 during pressurizing unfolds in a continuous and regular way. As can be seen from FIG. 4 and FIG. 5, the second rod 9 can telescope into and out from the first rod 8, thereby providing the telescopic guide 7 with a variable length that corresponds to the degree of expansion of the air cushion 6. Thus, when the air cushion 6 is not inflated, such as when the air cushion unit 4 is packaged, the second rod 9 of the telescopic guide 7 is completely, or almost completely, telescoped into the first rod 8, and when the air cushion 6 is inflated, the second rod 9 projects out from the first rod 8, i.e. the guide 7 is telescoped. Due to the variable length of the internal telescopic guide 7, the air cushion 6 is provided with a support that acts throughout the pressurizing of the air cushion 6. Providing the air cushion unit 4 with the internal telescopic guide 7 therefore prevents the irregular unfolding of the air cushion 6 and eliminates the possibility of any ball joint movements of the air cushion 6.

Before finishing the description of the operation of the telescopic guide, a few comments can be made. It should be understood that other ways of attaching the rods to the base plate and air cushion, respectively, could be employed. For example, the second rod could be inserted in a recess formed in the inner surface of the air cushion, or the second rod as well as the first rod could be attached to the air cushion and base plate, respectively, by gluing. It is also possible to let the rod that extends from the air cushion to be hollow, so that the other rod, which extends from the base plate, can be inserted therein. The important feature is that the air cushion unit according to the present invention is provided with an internal telescopic guide having a variable length that corresponds to the degree of expansion of the air cushion. For this purpose, it is also conceivable that the telescopic guide, as an alternative, comprises more than two rods that can telescope into and out from each other. Whether two or more rods are used for the telescopic guide, the number of rods as well as the length of each rod should preferably be chosen in such a way that when the telescopic guide is in its completely compressed state, the length of the telescopic guide should correspond to the cross-sectional height of the folded (packaged) air cushion. On the other hand, the maximum length of the telescopic guide should well cover the cross-sectional height of the completely inflated air cushion, so that a small overlap exists between the ends of the rods, thereby providing a stable and inflexible construction for the internal telescopic guide.

Although the present invention has been described with reference to a specific embodiment, also shown in the appended drawings, it will be apparent for those skilled in the art that many variations and modifications can be done within the scope of the invention as described in the specification and defined with reference to the following claims. For example, the guide may include at least three rods, the rods having increasing diameters, wherein at least two of the rods are hollow, and a rod having a smaller diameter is slidably positioned inside a rod having a larger diameter, so that telescopic action is achieved. As another example, the cushion may be inflated or filled with gases other than air, or with liquid(s).

What is claimed is:

1. An inflatable cushion assembly to apply pressure to a patient, comprising:
    a base plate,
    an inflatable cushion adapted to apply pressure to a wound, the inflatable cushion defining an enclosed interior space which is configured to be pressurized,
    two extensions connected to the base plate,
    at least one belt fastener, connected to at least one of the extensions, for receiving a belt to hold the inflatable cushion against the patient, and
    a telescopic guide inside the interior space, and coupled to, the cushion,
    wherein the telescopic guide expands and contracts in a direction perpendicular to the base plate when the interior space is pressurized.

2. An inflatable cushion assembly according to claim 1, wherein the telescopic guide expands and contracts in a direction perpendicular to the base plate in response to inflation and deflation of the inflatable cushion.

3. An inflatable cushion assembly according to claim 1, wherein the cushion is dome shaped.

4. An inflatable cushion assembly according to claim 1, wherein the cushion protrudes from the inflatable cushion assembly.

5. An inflatable cushion assembly according to claim 1, further comprising a belt.

6. An air cushion assembly comprising
    a base plate and an inflatable air cushion attached to the base plate and adapted to apply pressure to a wound, the inflatable air cushion defining an enclosed interior space which is configured to be pressurized, and two extensions connected to the base plate,
at least one belt fastener, connected to at least one of the extensions, for receiving a belt to hold the inflatable air cushion against the patient,
wherein the air cushion assembly comprises an internal telescopic guide, inside the interior space and coupled to the air cushion, having a first end and a second end, the first end being attached to the base plate and the second end being attached to the top of the air cushion, wherein the telescopic guide expands and contracts in a direction perpendicular to the base plate when the interior space is pressurized.

7. An air cushion assembly according to claim 6, wherein the telescopic guide comprises two rods, wherein the first rod is hollow and the second rod is slidably positioned inside the first rod, so that telescopic action of the telescopic guide is achieved.

8. An air cushion assembly according to claim 6, wherein the telescopic guide comprises at least three rods, wherein the rods have increasing diameters and at least two rods are hollow, and wherein a rod having a smaller diameter is slidably positioned inside a rod having a larger diameter, so that telescopic action of the telescopic guide is achieved.

9. An air cushion assembly according to claim 8, wherein a shortest length of the telescopic guide corresponds to a cross-sectional height of the air cushion in a folded state, and a longest length of the telescopic guide at least is as long as a cross-sectional height of the air cushion in a completely inflated state.

10. An air cushion assembly according to claim 6, wherein a shortest length of the telescopic guide corresponds to a cross-sectional height of the air cushion in a folded state, and a longest length of the telescopic guide at least is as long as a cross-sectional height of the air cushion in a completely inflated state.

11. An air cushion assembly according to claim 6, wherein the telescopic guide expands and contracts in a direction perpendicular to the base plate in response to inflation and deflation of the inflatable air cushion.

12. An assembly according to claim 6, further comprising a belt.

13. An inflatable cushion assembly to apply pressure to a patient, comprising:
    two extensions;
    a base plate with a device to releasably attach to the two extensions;
    at least one belt fastener, connected to at least one of the extensions, for receiving a belt;
    an inflatable cushion adapted to apply pressure to a patient by applying pressure to a wound; and
    a telescopic guide in an enclosed interior space of the cushion which is configured to be pressurized, and coupled to, the cushion;
    wherein the telescopic guide expands and contracts in a direction perpendicular to the base plate.

14. An inflatable cushion assembly according to claim 13, wherein the telescopic guide expands and contracts in a direction perpendicular to the base plate in response to inflation and deflation of the inflatable cushion.

15. An assembly according to claim 13, further comprising a belt.

16. An air cushion assembly comprising:
    a base plate, two extensions, a device to releasably attach the base plate to the two extensions, at least one belt fastener, connected to at least one of the extensions, for receiving a belt, and an inflatable air cushion attached to the base plate and adapted to apply pressure to a patient by applying pressure to a wound, wherein the inflatable air cushion comprises an internal telescopic guide, in and coupled to the air cushion, having a first end and a second end, the first
    end being attached to the base plate and the second end being attached to the top of the air cushion, wherein the telescopic guide expands and contracts in a direction perpendicular to the base plate.

17. An air cushion assembly according to claim 16, wherein the telescopic guide expands and contracts in a direction perpendicular to the base plate in response to inflation and deflation of the inflatable air cushion.

18. An assembly according to claim 16, further comprising a belt.

19. An air cushion unit comprising:
    a base plate, with a device to releasably attach the base plate to two extensions, at least one belt fastener, connected to at least one of the extensions, for receiving belt, and
    a dome shaped inflatable air cushion attached to the base plate and adapted to apply pressure to a patient by applying pressure to a wound,
    wherein the inflatable air cushion comprises an internal telescopic guide, in and coupled to the air cushion, having a first end and a second end, the first end being attached to the base plate and the second end being attached to the top of the air cushion such that the telescopic guide expands and contracts in a direction perpendicular to the base plate in response to inflation and deflation of the inflatable air cushion.

20. An air cushion unit according to claim 19, wherein the dome shaped inflatable air cushion is hemisphere shaped.

* * * * *